United States Patent [19]

Pikarski et al.

[11] Patent Number: 4,970,343

[45] Date of Patent: Nov. 13, 1990

[54] PROCESS FOR PURIFYING DINITROANILINE HERBICIDES

[75] Inventors: Michael Pikarski, Ramat-Gan; Edmund Dykman, Ashdod, both of Israel

[73] Assignee: Agan Chemical Manufacturers Ltd., Ashdod, Israel

[21] Appl. No.: 61,660

[22] Filed: Jun. 15, 1987

[30] Foreign Application Priority Data

Jun. 26, 1986 [IL] Israel ........................................ 79248

[51] Int. Cl.$^5$ .................. C07C 209/84; C07C 209/90
[52] U.S. Cl. ........................................ 564/437; 564/5
[58] Field of Search .................... 564/437, 441, 112, 5

[56] References Cited

U.S. PATENT DOCUMENTS

| | | | |
|---|---|---|---|
| 4,127,610 | 11/1978 | Eizenber | 260/582 |
| 4,331,468 | 5/1982 | Williams | 71/121 |
| 4,537,992 | 8/1985 | Pikarski et al. | 564/437 |

*Primary Examiner*—Richard L. Raymond
*Assistant Examiner*—Peter G. O'Sullivan
*Attorney, Agent, or Firm*—Cushman, Darby & Cushman

[57] ABSTRACT

A one-step process for the preparation of nitrosamine-free dinitroaniline herbicides which involves contacting the crude dinitroaniline herbicide in the liquid state, after removal of excess amine, with an effective quantity of a hydrobromide salt of a p-amino benzoate ester, optionally in the presence of such an ester, passing a gaseous stream of air therethrough or applying a reduced pressure so as to essentially remove water present, resulting in an essentially nitrosamine-free product.

18 Claims, No Drawings

PROCESS FOR PURIFYING DINITROANILINE HERBICIDES

The present invention concerns a method of removing nitrosamine impurities from herbicides. The present invention particularly concerns a simple and inexpensive method of removing nitrosamine impurities from dinitroaniline herbicides using very small amounts of a hydrobromide salt of an amino-benzoate ester alone or in combination with such amino benzoate ester.

Background of Invention

N-nitroso compounds, particularly alkyl nitrosamines have been identified as carcinogens for a wide range of mamalian species. Nitrosamines have been detected in many kinds of products such as pharmaceuticals, pesticides, cutting oils, cigarette smoke and foods like cheese, fish, spices, etc.

Several classes of herbicides are known to contain small amounts of nitrosamine impurities. Thus, for example, substituted dinitroaniline derivatives and dimethylamine salts of phenoxyalkanoic acid are major herbicides affected by this problem.

In the case of dinitroaniline derivatives, nitrosamine are believed to be formed by the reaction of the residual nitrosating agents left over from the nitration step, with the amine used in the subsequent ammination step.

For a number of years now pesticide manufacturers have been trying to reduce as much as possible the nitrosamine impurities in their products. Originally, trifluralin, for example, contained from between 15 to 300 ppm nitrosamine but because of the carcinogenic problem, the Environmental Protection Agency(EPA) in the U.S.A. limited the allowable concentration of nitrosamine to be 1 ppm. Most recently this limit was reduced even further, to 0.5 ppm. This, of course, put a great burden upon dinitroaniline producers to find ways of avoiding or eliminating such trace impurities in their products.

Another problem which came to light concerning dinitroaniline herbicides such as trifluralin was, that product which immediately after manufacture complied with the EPA requirement, was found to have increased nitrosamine content, as much as tenfold, when stored for long periods of time such as during overseas shipping, or when formulated into agriculturally useful formulations. It is believed that prolonged storage and particularly subjecting the dinitroaniline to melting temperatures, as during the formulation process, causes formation of small amounts of nitrosamines.

The problem of complying with the EPA nitrosamine standard has thus become twofold. First of all, to reduce the concentration to less than 0.5 ppm and secondly to prevent formation of the nitrosamine with time or with further processing.

Basically there exist two approaches for reducing nitrosamine content. One method is to eliminate or deactivate the nitrosating agent before it can react with any amine. This approach was taken by U. S. Pat. No. 4,120,905, which discloses the entraining of nitrosating agents from 4-chloro-3,5-dinitro benzo-trifluoride in the presence of a gas and a base. Similarly, German Offenlegungsschrift No. 2,926,946 discloses purification of the dinitro benzene intermediate from nitrosating agents by crystallization. U.S. Pat. No. 4,331,468 teaches the prevention of nitrosamine formation by the addition of monoalkanolamine retarding agent.

Another method for overcoming the nitrosamine problem is to decompose the already formed nitrosamines into harmless products. This method is applied by U.S. Pat. No. 4,226,789; which disclosed the reduction of nitrosamine content in dinitroanilines by heating the latter with either concentrated hydrochloric acid or HCl gas. This process requires substantial quantities of HCl with comcomitant additional work up of neutralization, washing and drying.

Similarly, U.S. Pat. No. 4,127,610 disclosed the reduction of nitrosamines in dinitroaniline herbicides by treating the latter with molecular bromine or molecular chlorine. However, the use of 10 per cent bromine was also reported to cause side reactions such as polymerization. In addition, extended exposure of the dinitroanilines with the denitrosation products under the reaction conditions was reported to result in the formation of further nitrosamines.

Recently, U.S. Pat. No. 4,537,992 disclosed the removal of nitrosamines from dinitroaniline herbicides by treating the latter with haloacetyl halides or amino benzoate esters.

SUMMARY OF THE INVENTION

We have unexpectedly found an inexpensive, one-step process for the production of essentially nitrosamine-free dinitroaniline herbicides which comprises contacting in the liquid state, the crude dinitro aniline herbicide resulting after removal of excess amine with an effective quantity of a hydrobromide salt of an ester having the formula

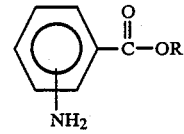

wherein R is a lower alkyl group;
optionally in the presence of such an ester, passing a gaseous stream therethrough or applying a reduced pressure so as to essentially remove water present, resulting in an essentially nitrosamine-free product.

The lower alkyl groups falling within this invention are p-aminoethyl benzoate, p-amino-methyl benzoate, p-amino-propylbenzoate, o-amino-methyl benzoate, o-amino-ethyl benzoate, o-amino-butyl benzoate, m-amino-methyl benzoate, m-amino-ethyl benzoate, m-aminopropyl benzoate, etc. with the p-amino-ethyl benzoate being most preferred.

The hydrobromide salt of the ester may be initially added in an amount of from 0.05% to 1.00% and preferably 0.10%.to 0.3% by weight of the dinitroaniline herbicide. The hydrobromide salt of the ester may be added directly to the dinitroaniline herbicide. Alternatively, it may be formed in situ by concurrently adding hydrobromic acid and the amino benzoate ester or by adding one reagent after the other.

By liquid state there is intended to mean the crude dinitroaniline herbicide in the form of a solution, a suspension, or as a melt.

The effectiveness of the hydrobromide salt of the amino benzoate ester is enhanced if it is added in the presence of free ester. The mixture of hydrobromide salt of the amino benzoate ester and free ester is usually added at an initial mole ratio of 1:0.01 to 1:5 and preferably 1:0.1 to 1:3 respectively.

A reaction time of one to two hours is usually sufficient to afford the substantial reduction in the nitrosamine concentration from about 1,000 ppm or less. In many cases the nitrosamine concentration is reduced to less than 0.5 ppm. The reaction is kept as homogeneous as possible by heating the dinitro-aniline herbicide preferably as a melt and being kept at a temperature of between 60° C. and 90° C.

Subsequent to adding the hydrobromide salt of the amino benzoate ester alone or in combination with free ester, a gas such as air or an inert gas is bubbled into the reaction mixture to remove water. Alternatively, the water may be removed by applying a reduced pressure.

Thus, the process of the present invention affords an inexpensive, one-step process for removing nitrosamines from crude, moist dinitroaniline herbicides. This process requires very small amounts of the hydrobromide salt of an amino benzoate ester with relatively short reaction times. In addition, the process of the present invention directly affords a product which requires no subsequent work-up such as neutralization, repeated washings and drying to remove excess acid or reagent as the case may be.

Nitrosamine containing herbicides for which the process of this invention is applicable, among others, are:(- the common names are in parenthesis)
5-(2-chloro-4-(trifluoromethyl)-phenoxy)-2-nitrobenzoic acid(acifluorfen);
N-butyl-N-ethyl-2,6-dinitro-4-(trifluoromethyl)benzenamine(benefin);
5-(2,4-dichlorophenoxy)-2-nitrobenzoic acid methyl ester(bifenox);
4-(1,1-dimethylethyl)-N-(1-methyl-propyl-.)-2,6-dinitrobenzenamine(butralin);
$N^3$,$N^3$-diethyl-2,4-dinitro-6-(trifluoromethyl)-1,3-benzene-diamine (dinitramine);
2,4-dinitro-6-sec-butylphenol-(dinoseb);
N-ethyl-N-(2-methyl-2-propenyl)-2,6-dinitro-4-(trifluoromethyl)benzenamine-(ethalfluralin);
N-(2-chloroethyl)-2,6-dinitro-N-propyl-4-(trifluoromethyl) benzenamine-(fluchloralin);
4-(1-methylethyl)-2,6-dinitro-N,N-dipropylbenzenamine-(isopropalin);
4-(methylsulfonyl)-2,6-dinitro-N,N-dipropylbenzenamine-(nitralin);
2,4-dichloro-1-(4-nitrophenoxy)-benzene-(nitrofen);
4-(dipropylamine)-3,5-dinitrobenzenesulfonamide-(oxyzalin);
2-chloro-1-(3-ethoxy-4-nitrophenoxy)-4-(trifluoromethyl)benzene(oxyfluorofen);
N-(1-ethylpropyl)-3,4-dimethyl-2,6-dinitrobenzenamine-(pendimethalin);
2,4-dinitro-$N^3$,$N^3$-dipropyl-6-(trifluoromethyl)-1,3-benzenediamine(prodiamine);
N-(cyclopropylmethyl)-2,6-dinitro-N-propyl-4-(trifluoromethyl) benzenamine-(profluralin);
N-(4-dipropylamine)-3,5-dinitrophenyl)sulfonyl)-S,S-dimethylsulfilimine(prosulfalin);
2,6-dinitro-N,N-dipropyl-4-(trifluoromethyl)benzenamine-(trifluralin);

The analysis for nitrosamine concentration were all conducted by G.C using a thermal energy analyzer (TEA) as detector which has been developed for this purpose and described in J. Chromatog(1975)351.

While the invention will now be described in connection with certain preferred embodiments in the following examples it will be understood that it is not intended to limit the invention to these particular embodiments. On the contrary it is intended to cover all alternatives, modifications and equivalents as may be included within the scope of the invention as defined by the appended claims.

EXAMPLES 1–4

To determine the reduction of nitrosamine concentration in dinitroaniline herbicides according to the present invention the following series of experiments were conducted. To 100 g crude trifluralin kept at a temperature between 60° C. to 90° C. was added either the hydrobromide of p-amino ethyl benzoate alone or in combination with free p-amino ethyl benzoate, the reaction mixture was mechanically stirred for a half an hour and then air is bubbled through for an additional one to one and a half hours. The melt was analyzed for nitrosamines and cooled to directly yield trifluralin containing less than 0.5 ppm nitrosamine. The results are shown in Table 1. Similar results can be obtained with the herbicides mentioned above on pages 7-8 under equivalent conditions of reactions.

EXAMPLE 5

To 140 kg crude, wet trifluralin having an initial nitrosamine concentration of 54 ppm was added 420 g (0.3%)of the hydrobromide of p-amino ethyl benzoate and the mixture kept 80 ° C. for one hour. The nitrosamine concentration was then found to drop to 0.05ppm. The mixture was heated for an additional hour; and then dried by passing air through for two hours keeping at a temperature no greater than 100° C. This yielded trifluralin having a nitrosamine concentration of 0.05 ppm.

EXAMPLE 6

The method of Example 6 was followed, but the hydrobromide of p-amino ethyl benzoate was formed in situ by adding 350 g p-aminoethyl benzoate and 235 g hydrobromic acid (47%). The mixture was heated for one hour at 90° C.; whereby the nitrosamine concentration was found to drop from 54 ppm to 0.2 ppm. The mixture was then dried in air for two hours to yield trifluralin having a nitrosamine concentration of 0.1 ppm.

TABLE 1

| Example | Trifluralin | Type of Reagent | Concentration (Percent) | Final Concentration of Nitrosamine (ppm) |
|---|---|---|---|---|
| 1 | dry | Benzocaine-HBr[a] | 0.3 | 0.1[c] |
| 2 | wet | Hydrobromic acid Benzocaine | 0.08[b] 0.2 | 0.3[c] |
| 3 | dry | Hydrobromic acid Benzocaine | 0.04[b] 0.2 | 0.07[c] |
| 4 | dry | Hydrobromic acid Benzocaine | 0.08[b] 0.2 | 0.2[d] |

[a]Benzocaine = p-amino ethyl benzoate
[b]Based on 100% hydrobromic acid
[c]Compared with an initial nitrosamine concentration of 50 ppm
[d]Compared with an initial nitrosamine concentration of 213 ppm.

COMPARATIVE EXAMPLE 1

To wet, crude, trifluralin was added 0.5% hydrochloric acid(based on 100% acid). After a reaction time of 2 hours (as done in Examples 1-3) the nitrosamine content had only dropped from 50 ppm to 40 ppm.

COMPARATIVE EXAMPLE 2

Following the method of Example 2, but using 0.5% hydrochloric acid and 0.2% benzocaine on wet, crude trifluralin, the nitrosamine content after a 2 hour reaction time had dropped from 50 ppm to 2.5 ppm. Thus, Comparative Examples 1 and 2 clearly show that using the reagents of the prior art under the conditions of the present invention will give results which are unacceptable since the nitrosamine content is still way above the 0.5 ppm maximum permitted by the EPA.

We claim:

1. A one-step process for the production of essentially nitrosamine-free dinitroaniline herbicides comprising contacting in the liquid state crude dinitroaniline herbicide resulting after the removal of excess amine with an effective quantity of a hydrobromide salt of an amino benzoate ester having the formula:

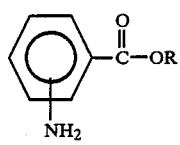

wherein R is a lower alkyl group;
optionally in the presence of such an ester, passing a gaseous stream therethrough or applying a reduced pressure so as to essentially remove water present, resulting in an essentially nitrosamine-free product.

2. A process in accordance with claim 1 wherein the nitrosamine impurities are lowered to less than 0.5 ppm.

3. A process in accordance with claim 1 wherein the crude dinitroaniline herbicide contains up to one per cent water.

4. A process in accordance with claim 1 wherein the hydrobromide salt of the ester is initially added in the range of 0.05% to 1.0%, by weight calculated on the dinitroaniline herbicide.

5. A process in accordance with claim 1 wherein the dinitroaniline herbicide is trifluralin.

6. A process in accordance with claim 1 wherein the amino benzoate ester is chosen from the group consisting of p-amino ethyl benzoate, p-amino-methyl benzoate, p-amino propylbenzoate, o-amino-methyl benzoate, o-amino ethyl benzoate, o-amino-butyl benzoate, m-amino methyl benzoate, m-amino ethyl benzoate, and m-amino propyl benzoate.

7. A process in accordance with claim 6 wherein the ester is p-amino ethyl benzoate.

8. A process in accordance with claim 1 wherein the initial mole ratio of hydrobromide salt to ester is 1:0.01 to 1:5, respectively.

9. A one-step process for the production of essentially nitrosaminefree trifluralin comprising contacting a melt of the crude trifluralin resulting after the removal of excess amine with from 0.05% to 1.0 %, by weight calculated on the trifluralin, of the hydrobromide salt of p-amino ethyl benzoate optionally in the presence of p-amino ethyl benzoate, passing a stream of air therethrough to essentially remove water present, resulting in essentially nitrosamine-free trifluralin.

10. A process in accordance with claim 9 wherein the nitrosamine impurities are lowered to less than 0.5 ppm.

11. A process in accordance with claim 9 wherein the initial mole ratio of p-amino ethyl benzoate hydrobromide to p-amino ethyl benzoate is 1:0.01 to 1:5 respectively.

12. A process in accordance with claim 1 wherein the dinitroaniline herbicide product is stabilized against the further formation of nitrosamines by the presence of an ester as defined in claim 1.

13. A process in accordance with any of claims 1 through 8, wherein the initial concentration of nitrosamines is greater than about 5 ppm.

14. A process in accordance with any of claims 9 through 11, wherein the initial concentration of nitrosamines is greater than about 5 ppm.

15. A process in accordance with claim 4 wherein the hydrobromide salt of the ester is initially added in the range of 0.1% to 0.3% by weight calculated on the dinitroaniline herbicide.

16. A process in accordance with claim 8 wherein the initial mole ratio of hydrobromide salt to ester is 17. A process in accordance with claim 9 wherein said melt of the crude trifluralin resulting after removal of excess amine is contacted with from 0.1% to 0.3%, by weight calculated on the trifluralin, of the hydrobromide salt of p-amino ethyl benzoate.

18. A process in accordance with claim 11 wherein the initial mole ratio of p-amino ethyl benzoate hydrobromide to p-amino ethyl benzoate is 1:0.1 to 1:3 respectively.

* * * * *